United States Patent [19]

Berger

[11] Patent Number: 4,575,339
[45] Date of Patent: Mar. 11, 1986

[54] PROSTHESIS SUBSTRUCTURE
[76] Inventor: Robert P. Berger, 4421 Rochelle Pl, Encino, Calif. 91316
[21] Appl. No.: 621,852
[22] Filed: Jun. 18, 1984
[51] Int. Cl.[4] .............................................. A61C 13/00
[52] U.S. Cl. .................................. 433/167; 433/180; 433/200.1
[58] Field of Search ............... 433/200, 167, 191, 199, 433/202, 208, 209, 212, 213, 183, 180, 181, 182
[56] References Cited

U.S. PATENT DOCUMENTS

| | | | |
|---|---|---|---|
| 1,376,644 | 5/1921 | Russell | 433/180 |
| 2,799,933 | 7/1957 | Neustadter | 433/183 |
| 2,948,963 | 8/1960 | Neustadter | 433/183 |
| 4,231,740 | 11/1980 | Shoher et al. | 433/208 |

Primary Examiner—John J. Wilson
Attorney, Agent, or Firm—Allan M. Shapiro

[57] ABSTRACT

Prosthesis substructure for ceramic coating is configured for reduced metallic body volume, increased vertical loading strength and increased surface bonding area for ceramic bond. This is accomplished by configuring the substructure with generally triangular truss configuration.

16 Claims, 7 Drawing Figures

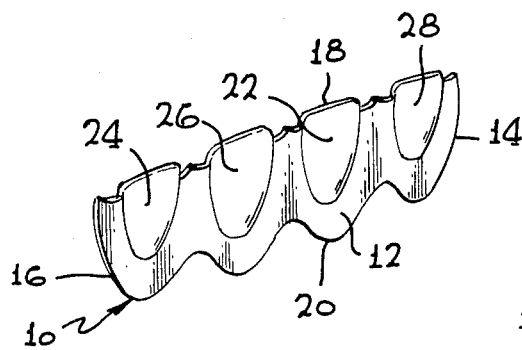
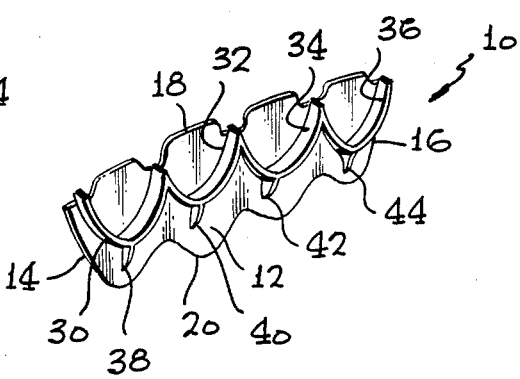
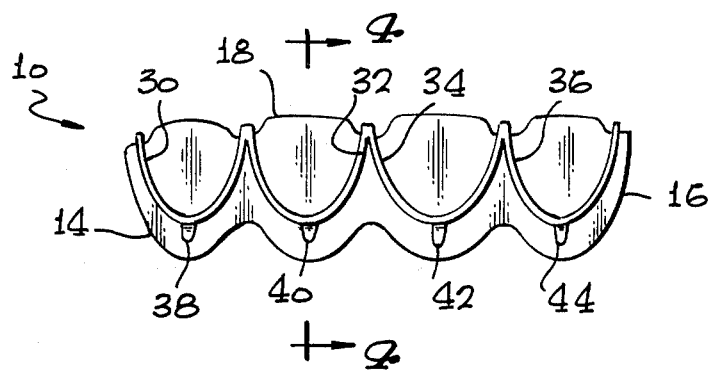
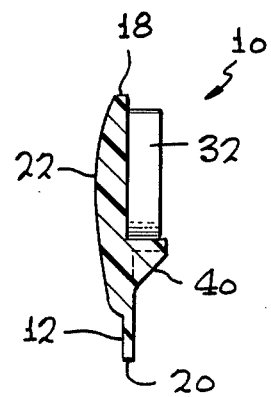
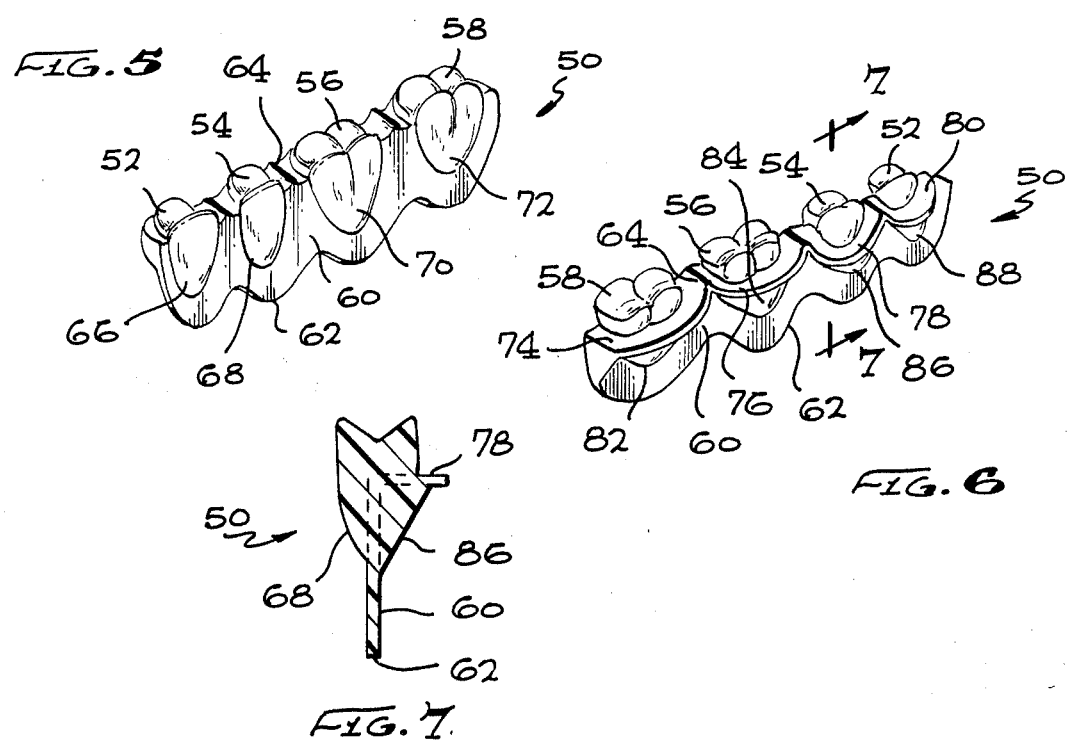

PROSTHESIS SUBSTRUCTURE

BACKGROUND OF THE INVENTION

This invention is directed to a dental prosthesis substructure wherein the substructure has a reduced metallic body volume for economy, increased ceramic bonding area for secure ceramic structure and increased vertical loading strength so that it can withstand normal forces without bending and breaking the porcelain.

Most prior art dental prosthesis substructures have followed the configuration of nature. Molds are taken of the original tooth shape, and these shapes are reduced in size to accommodate the equivalent of porcelain surface. In this way, a prosthesis having substantially the original tooth configuration is produced. The problems of such prostheses include the fact that there is a large volume of substructure metal therein. This metal is expensive, and as a consequence, the dental restoration can be reduced in cost by reducing the volume of metal therein. In addition, the original configuration is not the best as far as strength is concerned. The force loadings on the original teeth are almost directly from the occlusal surfaces through the root into the jaw bone. However, in a prosthesis, especially one for several teeth, the occlusal loads are transmitted laterally across the prosthesis to the ends, in the case of a bridge. The original tooth shape configuration is not an optimum shape for transmitting these loads in that direction.

U.S. Pat. No. 4,231,740 to Shoher, et al. teaches a dental metal substructure composed of a framework of relatively thin metal members interconnected to form concavities. Porcelain fills and surrounds the network. While the patent speaks of configuring the framework to be sufficiently rigid for the purpose, it has been found that the open network substructure is not sufficiently strong for bridgework and the like. Furthermore, the open interior makes it difficult to apply the ceramic to the desired final configuration. Thus, this open network substructure has not been successful.

Thus, there is need for a prosthesis substructure of specific design to provide adequate vertical loading strength with a reduced body volume.

SUMMARY OF THE INVENTION

In order to aid in the understanding of this invention, it can be stated in essentially summary form that it is directed to a dental prosthesis substructure which has a central generally flat member lying so that mastecatory forces are generally in the plane of the flat member. Strengthening flanges are formed on at least one side of the flat member, with some of the flanges joining each other in truss-like configuration to increase the strength of the metallic substructure, decrease its volume and increase its surface bonding area for the application of porcelain thereon.

It is, thus, an object and advantage of this invention to provide a metal prosthesis substructure which is of reduced body volume to conserve metal, increase vertical loading strength in the direction of mastication forces to inhibit excessive bending and breaking, and provide increased surface bonding area for the bonding of porcelain thereon so that the porcelain is firmly bonded.

It is another object and advantage of this invention to provide a prosthesis substructure which is initially configured in wax so that it can be shaped and positioned and thereafter cast by the investment casting process to provide a metallic prosthesis substructure configured for a particular prosthetic purpose and of desirable configuration for strength, economy and long life.

It is a further purpose and advantage of this invention to provide a prosthesis substructure which is configured to receive porcelain which is realistically shaped to provide a realistic dental appearance and is sufficiently strong to withstand normal mastication forces.

It is a further object and advantage of this invention to provide a dental prosthesis substructure which is formed of members and flanges which join in a truss-like configuration to provide strength in the prosthesis to resist normal mastication forces, and at the same time, minimize the volume of the prosthesis substructure.

The features of the present invention which are believed to be novel are set forth with particularity in the appended claims. The present invention, both as to its organization and manner of operation, together with further objects and advantages thereof, may be best understood by reference to the following description, taken in conjunction with the accompanying drawings.

BRIEF DESCRIPTION OF THE DRAWINGS

FIG. 1 is a perspective view of the labial side of a dental prosthesis substructure suitable for producing an incisor dental prosthesis, configured in accordance with this invention.

FIG. 2 is a perspective view of the lingual side thereof.

FIG. 3 is an enlarged elevational view of the lingual side of the prosthesis substructure shown in FIGS. 1 and 2.

FIG. 4 is a further enlarged section taken generally along the line 4—4 of FIG. 3.

FIG. 5 is a perspective view of a dental prosthesis substructure showing the labial side of the substructure which carries two molars and two bicuspids, configured in accordance with this invention.

FIG. 6 is a perspective view of the lingual side of the prosthesis of FIG. 5.

FIG. 7 is an enlarged section taken generally along the line 7—7 of FIG. 6.

DESCRIPTION OF THE PREFERRED EMBODIMENTS

FIGS. 1, 2, 3 and 4 show a first preferred embodiment of the dental prosthesis substructure of this invention wherein the substructure is configured for the production of a prosthesis having incisors. This substructure is generally indicated at 10 in those figures. The prosthesis substructure 10 is a 3-dimensional body having a vertical dimension in the direction of mastication forces, which is the upright direction in FIGS. 1 through 4. The prosthesis substructure has a width dimension in the direction around the dental arch, in the left-to-right direction of FIG. 3. In addition, the prosthesis substructure has a thickness dimension in the lingual-to-labial direction and in the left-to-right direction in FIG. 4. The material of the dental prosthesis substructure 10 illustrated in FIGS. 1 through 4 starts as a wax master for joining with other parts to correspond to the individual dental prosthesis for a particular dental procedure. When the wax model is built up to the desired configuration and shape, it is used as a wax master in the investment casting process to form the metallic prosthesis substructure upon which porcelain is placed and fired to form the dental prosthesis.

In order to form the optimum dental prosthesis, the prosthesis must be strong, must be economic of materials, and must be structured so that it has a long life. Each of these features can be enhanced by the proper configuration of the substructure. As seen in FIGS. 1 through 4, substructure 10 has a fairly flat central member 12 which extends from the left end 14 to the right end 16, as seen from the lingual side in FIGS. 2 and 3. Furthermore, the flat central member extends from the upper, occlusal edge 18 to the lower, gingival edge 20. As seen in FIG. 4, the central member 12 is not quite flat, but the upper portion is thickened by having an incisor tooth-shaped panel 22 formed therewith, shaped somewhat like the labial surface of an incisor. As is seen in FIG. 1, in the illustrated embodiment, there are four such panels 22, 24, 26 and 28 formed on the front of the central member to represent a prosthesis which has four incisors thereon. The flat central member extends the whole width of the substructure and does not terminate between tooth margins in the widthwise direction. The panels are built up on the central member to aid in later shaping of the porcelain in the area where it is most visible. The flat plate represented by the flat central member 12 has a considerable bending strength in the direction of mastication forces, in the plane of the flat central member in a direction crosswise to its length. The lower, gingival edge 20 may be scalloped, as shown, to produce a gingival margin which is configured to provide the desired shape in the dental prosthesis. As is seen in FIG. 4, the lower portion of the flat central member 12 is turned slightly out, in the labial direction, adjacent the gingival margin.

In order to enhance the strength of the dental prosthesis, webs are secured to the lingual side thereof. As is seen in FIGS. 2 and 3, narrow webs 30, 32, 34 and 36 are secured to the lingual side of the flat central member. These webs are of generally U-shape, but with the arms of the U converging toward the closed bottom, with a decreasing radius of curvature to the bottom of the U-shaped web so that the web is almost V-shaped with a curved lower point. At their upper terminations, the arms of the webs are joined to the arms of adjacent webs. This structure is in the nature of a triangular truss, which provides considerable additional strength to the flat central member in the direction of mastication forces, generally in the plane of the flat central member and crosswise through its length dimension. In view of the fact that the webs are curved instead of straight, a small buttress at the downwardly directed apex of each web strengthens the apex. The buttresses are indicated at 38, 40, 42 and 44.

In addition to the important feature of strenghtening the central member, the webs and buttresses also increase the contact area of porcelain which is laid onto the sustrate. After the dental prosthesis substrate is produced in metal by the investment casting process, porcelain is painted thereon to produce an exterior configuration which is the desired configuration for the dental prosthesis. Thereupon, the substrate and its porcelain coating are fired to cure the porcelain, to complete the prosthesis. During the application of the porcelain paste, adhesion to the prosthesis substructure is necessary. Furthermore, during the firing process, adhesion must be maintained. An increased area on the substructure surface aids in the adhesion both in the paste stage and in the fired state. Furthermore, the substructure and porcelain must be configured so that during the high temperatures of firing, adhesion is not lost and cracking of the porcelain does not occur. The relatively flat central member 12 of the present structure, together with its webs which produce the truss structure, increase the area of porcelain adhesion and do not provide enclosed spaces completely surrounded by metallic substructure which increase the chance of cracking of the porcelin during temperature cycling.

While the dental prosthesis substructure illustrated in FIGS. 1 through 4 shows a four incisor tooth prosthesis, it is clear that it is useful for producing the metal prosthesis substructure for any kind of dental restoration having a porcelain superstructure, for example, a crown, a pontic, a bridge and a denture tooth.

To illustrate this wide utility of the dental prosthesis substructure of this invention, FIGS. 5, 6 and 7 illustrate a dental prosthesis substructure 50 which incorporates therein two bicuspids and two molars. In similar fashion, the prosthesis substructure starts as a wax master, and in that form, is shaped and joined to other wax master substructure to create a master of the desired size and configuration. For example, one or more incisors of the dental prosthesis substructure 10 might be attached to the bicuspid end of the dental prosthesis substructure 50. When the wax master dental prosthesis substructure is complete, it is mounted upon sprues and gates and investment material is poured therearound. After removal of the wax master, metal is poured into the investment mold to produce a metallic dental prosthesis substructure configured as required, for example, as shown as the dental prosthesis substructure 50 in FIGS. 5 through 7. Bicuspid substructures 52 and 54 as well as molar substructures 56 and 58 are shown from the labial side in FIG. 5 and from the lingual side in FIG. 6. The prosthesis substructure 50 has a flat central member 60 which extends from the lower gingival margin edge 62 to an upper edge 64 between the teeth prostheses. The flat central member lies in a position to take the mastication forces edgewise through the central member. On the labial side of the central member, panels 66 and 68 are added to provide a basic configuration for the labial sides of the prosthesis bicuspids, and panels 70 and 72 are provided for the same purpose with respect to the molars. These panels give some shape to the labial side so that porcelain can be painted thereon and a tooth-like shape can be created without substantial variations in the porcelain thickness and aid the technician in producing a tooth-like surface.

On the lingual side illustrated in FIG. 6, U-shaped webs 74, 76, 80 and 80 are illustrated as attached to the top edge of central member 60 and extending in the lingual direction. The U-shaped webs are fairly shallow in the direction of the bend of the U, as compared to the webs in FIG. 5, but perform the same function of strengthening the central member 60 in the direction of mastication forces and in the direction of bending of the central member in a direction normal to the mastication forces and normal to the length of the central member. In view of the relatively shallow bend of the U-shaped webs, larger buttresses are employed to hold the webs in place. These buttresses are illustrated at 82, 84, 86 and 88 in FIG. 6 and buttress 86 is also shown in FIG. 7. These larger buttresses also serve to strengthen the webs because a substantial portion of the individual tooth prosthesis substructure is mounted upon the webs. That portion which is not in the panels on the labial side is mounted on the top of the webs, and each tooth substructure on the webs is completely backed up by a buttress so that all mastication forces onto the tooth substructure is transferred into the flat central member. It is seen in both FIGS. 5 and 6 that the webs join together in cusps between the individual tooth prostheses substructures.

While the central members have been described and illustrated as being flat, when the dental prosthesis substructure is in the wax master form, the form is built up by attaching together appropriate portions and shaping the portions into the shape of the dental arch in which the prosthesis will be applied. This means that the central member is not planar, but is curved to fit the arch. When shaped in that way, the central member lies in a direction that it receives the mastication forces edgewise of the central member and the U-shaped webs provide resistance to bending of the prosthesis substructure in the direction of the mastication forces and in the lingual-to-labial direction. It is appreciated that when the wax master of the prosthesis substructure is created and shaped, when several portions are joined together, the central members are endwise joined and the webs are endwise joined so that the strength characteristics are transmitted across such joints, and no joints occur in the metallic prosthesis substructure which is investment-cast from the integrated and shaped wax master.

After the production of the metallic dental prosthesis substructure, it is painted with porcelain to the configuration desired. The central member and webs of the prosthesis substructure provide a substantial area for porcelain adhesion. Furthermore, the substructure has metal therein which transfers the mastication forces from the porcelain chewing surfaces through to the U-shaped webs and central member. The tooth-like shapes in the substructure are not an attempt to produce the tooth shape, but to transfer the mastication forces. For this reason, the entire substructure narrows down to the central member in the direction away from the portion toward the mastication surfaces. In this way, 3-dimensional prosthesis substructure is produced which has reduced body volume in order to economize on metal, has increased vertical loading strength in the direction of the mastication forces, and has increased surface bonding area for the adhesion of porcelain thereto. In this way, a desirable prosthesis substructure is created.

This invention has been described in its presently contemplated best mode, and it is clear that it is susceptible to numerous modifications, modes and embodiments within the ability of those skilled in the art and without the exercise of the inventive faculty. Accordingly, the scope of this invention is defined by the scope of the following claims.

What is claimed is:

1. A dental prosthesis substructure comprising:
   a central member having a buccal and a lingual side, said central member having a width extending across a plurality of tooth spaces, a height extending from a gingival margin to an occlusal edge, and a thickness between said sides, said central member of said prosthesis substructure being for positioning on the dental arch with its height direction in the direction of principal mastication forces; and
   a plurality of U-shaped webs integrally formed with said central member and extending from the lingual side thereof, said U-shaped webs being oriented for strengthening the central member against bending of said central member both in the height direction and thickness direction.

2. The prosthesis substructure of claim 1 wherein said U-shaped webs are joined together.

3. The prosthesis substructure of claim 2 wherein said U-shaped webs are joined together between tooth spaces.

4. A dental prosthesis substructure comprising:
   a central member, said central member having a width extending across a plurality of tooth spaces, a height extending from a gingival margin to an occlusal edge, and a thickness, said central member of said prosthesis substructure being for positioning on the dental arch with its height direction in the direction of mastication forces; and
   a plurality of U-shaped webs integrally formed with said central member on the lingual side of said central member, said U-shaped webs being oriented for strengthening the central member against bending of said central member both in the height direction and thickness direction.

5. A dental prosthesis substructure comprising:
   a central member, said central member having a width extending across a plurality of tooth spaces, a height extending from a gingival margin to an occlusal edge, and a thickness, said central member of said prosthesis substructure being for positioning on the dental arch with its height direction in the direction of mastication forces; and
   a plurality of U-shaped webs integrally formed with said central member on the lingual side of said central member, said U-shaped webs being joined together between tooth spaces, said U-shaped webs being oriented for strengthening the central member against bending of said central member both in the height direction and thickness direction.

6. A dental prosthesis substructure comprising:
   a central member having a buccal and a lingual side, said central member having a width extending across a plurality of tooth spaces, a height extending from a gingival margin to an occlusal edge, and a thickness between said sides, said central member of said prosthesis substructure being for positioning on the dental arch with its height direction in the direction of principal mastication forces;
   a plurality of U-shaped webs integrally formed with said central member and extending from the lingual side thereof, said U-shaped webs being oriented for strengthening the central member against bending of said central member both in the height direction and thickness direction;
   a buttress adjoining the apex of said U-shaped member with said central member, said buttress being integrally formed with said central member and said U-shaped web, said buttress being oriented to transfer principal mastication forces from said web to said central member.

7. The prosthesis substructure of claim 6 wherein said U-shaped webs are joined together between tooth spaces.

8. A dental prosthesis substructure comprising:
   a central member, said central member having a width extending across a plurality of tooth spaces, a height extending from a gingival margin to an occlusal edge, and a thickness, said central member of said prosthesis substructure being for positioning on the dental arch with its height direction in the direction of mastication forces;
   a plurality of U-shaped webs integrally formed with said central member on the lingual side of said central member, said U-shaped webs being oriented for strengthening the central member against bending of said central member both in the height direction and thickness direction; and a buttress adjoining the apex of said U-shaped member with said central member, said buttress being integrally formed with said central member and said U-shaped web.

9. A dental prosthesis substructure comprising:

a central member, said central member having a width extending across a plurality of tooth spaces, a height extending from a gingival margin to an occlusal edge, and a thickness, said central member of said prosthesis substructure being for positioning on the dental arch with its height direction in the direction of mastication forces;

a plurality of U-shaped webs integrally formed with said central member on the lingual side of said central member, said U-shaped webs being oriented for strengthening the central member against bending of said central member both in the height direction and thickness direction; and a panel formed on the labial side of said central member with a panel corresponding to each tooth position on said central member, one of said U-shaped webs being integrally formed with said central member on the lingual side thereof opposite each of said panels.

10. The prosthesis substructure of claim 9 wherein each of said U-shaped webs is adjoined to an adjacent U-shaped web adjacent the occlusal edge of said central member.

11. The prosthesis substructure of claim 9 wherein there is a buttress integrally formed between the apex of said U-shaped web and said central member on the lingual side of said prosthesis substructure.

12. A dental prosthesis substructure comprising:

a central member having a width across a plurality of tooth spaces, a height from a gingival edge to an occlusal edge, and a thickness which is substantially uniform, said prosthesis substructure being unitarily formed of metal;

a plurality of U-shaped webs secured to the lingual side of said central member, said U-shaped webs having their apexes directed toward said gingival margin and having their arms directed toward said occlusal edge, said arms being adjoined adjacent said occlusal edge, there being a U-shaped web for each of the tooth spaces on said central member.

13. The prosthesis substructure of claim 12 wherein there is a buttress formed between the apex of said U-shaped web and said central member.

14. The prosthesis substructure of claim 13 wherein there is a panel formed on the labial side of said central member opposite each of said U-shaped webs.

15. The prosthesis substructure of claim 12 wherein there is a panel formed on the labial side of said central member opposite each of said U-shaped webs.

16. A prosthesis having said prosthesis substructure of claim 12, wherein said substructure is coated all over with porcelain paste and is fired to produce a hard porcelain overall surface.

* * * * *